United States Patent [19]
Ruiz

[11] Patent Number: 5,868,779
[45] Date of Patent: Feb. 9, 1999

[54] APPARATUS AND METHODS FOR DILATING VESSELS AND HOLLOW-BODY ORGANS

[76] Inventor: Carlos E. Ruiz, 1747 N. Country La., Pasadent, Calif. 91107

[21] Appl. No.: 911,953

[22] Filed: Aug. 15, 1997

[51] Int. Cl.⁶ ................................................. A61M 29/00
[52] U.S. Cl. .......................................... 606/194; 606/192
[58] Field of Search ................................. 606/194, 192, 606/198, 191, 108; 604/96, 101, 103

[56] References Cited

U.S. PATENT DOCUMENTS

| | | |
|---|---|---|
| 2,701,559 | 2/1955 | Cooper . |
| 4,018,230 | 4/1977 | Ochiai et al. ............................ 128/344 |
| 4,702,252 | 10/1987 | Brooks et al. ........................... 128/344 |
| 4,998,539 | 3/1991 | Delsanti .................................. 128/898 |
| 5,221,261 | 6/1993 | Termin et al. ........................... 604/104 |
| 5,447,497 | 9/1995 | Sogard et al. ........................... 604/101 |
| 5,667,523 | 9/1997 | Bynon et al. ........................... 606/194 |
| 5,766,201 | 6/1998 | Ravenscroft et al. ................... 606/194 |
| 5,772,681 | 6/1998 | Leoni ...................................... 606/192 |

*Primary Examiner*—Michael Buiz
*Assistant Examiner*—Kevin Truong
*Attorney, Agent, or Firm*—Fish & Neave; Nicola A. Pisano

[57] ABSTRACT

Apparatus and methods for dilating a vessel or organ, especially a larger diameter vessel or organ, are provided using a catheter having a balloon element is disposed within a sheath having an expandable but non-compliant mesh region covering the balloon element. The sheath is selected from among a plurality of sheaths each having a mesh member that is expandable to a different predetermined expanded diameter, the mesh region preventing the balloon member from developing bulges during inflation and constraining the edges of the balloon from perforating the vessel in the event of perforation. The sheath, which extends to a proximal end of the catheter, is also employed to reduce the diameter of the balloon member following the dilatation procedure, thereby preventing the balloon from bunching up in the vessel or organ.

20 Claims, 2 Drawing Sheets

APPARATUS AND METHODS FOR DILATING VESSELS AND HOLLOW-BODY ORGANS

FIELD OF THE INVENTION

The present invention relates to apparatus and methods for dilating constrictions in vessels and hollow-body organs, such as the coronary arteries, the pulmonary artery and the aorta. More particularly, the present invention provides a device having a precisely controllable expanded diameter that enables a clinician to dilate a vessel or organ with a balloon using high pressures, and with reduced risk of rupture of the balloon or dissection of the vessel.

BACKGROUND OF THE INVENTION

Coronary artery disease is a leading cause of death in the United States today, and involves the accumulation of atherosclerotic plaque in the coronary arteries, resulting in ischemia of the heart. The disease, which is manifested as chest pain or angina, afflicts several million people in the United States.

A surgical method that has been used to treat this disease for more than thirty years is coronary artery bypass grafting (CABG), in which the patient's chest is opened and an obstructed artery replaced with a native artery harvested elsewhere or a synthetic graft. Such surgery creates significant trauma to the patient, requires long recuperation times, and poses serious risks of mortality. In addition, experience has shown that the bypass vessel or graft becomes obstructed with time, requiring further surgery.

More recently, minimally-invasive catheter-based therapies have been developed, such as percutaneous transluminal coronary angioplasty (PTCA). In PTCA, a mechanical dilatation device, generally a balloon catheter, is disposed across an obstruction in the patient's artery and then dilated to compress the plaque lining the artery to restore patency to the vessel. More recently, endoluminal prostheses, commonly called "stents," are deployed in the artery following the angioplasty procedure to retain the patency of the vessel.

Balloon dilatation devices generally employ either minimally-compliant balloons, which experience a relatively small increase in diameter when the balloon is expanded, or compliant balloons, which experience a relatively large increase in diameter in response to an increase in pressure, as described, for example, in U.S. Pat. No. 5,447,497 to Sogard et al. Non-compliant balloons are generally favored for angioplasty because they may be reliably expanded to a known size, whereas compliant balloons permit treatment over a larger range of diameters. In order to provide a mixture of the desirable characteristics of each of these types of balloons, dilatation devices have been designed, as described in U.S. Pat. No. 5,447,497, that include layers of both compliant and non-compliant material.

Other balloon dilatation devices have employed elastomer impregnated braided material or nets to constrain the inflated size of the device, such as described in U.S. Pat. No. 4,702,252 to Brooks et al. and U.S. Pat. No. 4,108,236 to Ochiai et al. Still other devices, such as described in U.S. Pat. No. 4,998,539 to Delsanti and U.S. Pat. No. 5,221,261 to Termin et al. include members for supporting a vessel following angioplasty. U.S. Pat. No. 4,998,539 describes a separately movable plaited net disposed over a balloon catheter. The plaited net is expanded against the interior of the vessel by the balloon during angioplasty, and temporarily remains in place after balloon deflation to prevent detachment of material from the vessel wall.

One disadvantage encountered in PTCA has been the inability to dilate certain types of stenosis without exceeding the limitations imposed on the balloon element by materials considerations. For example, most angioplasty catheters constructed from polyethylterephalate (PET) or polyethylene (both non-compliant materials), generally may not be pressurized above 22 atmospheres without risk of rupture. Rupture of the balloon element often may have fatal consequences, because it may cause dissection of the vessel and require an emergency thoracotomy to repair the dissected vessel.

Accordingly, if a stenosis cannot be disrupted using dilatation element pressures within the useful range of the dilatation element material, then the constriction must be addressed by other means, such as conventional bypass or grafting procedures.

A further drawback to previously known balloon dilatation devices is the relative small range of expanded diameters that such devices can achieve. For example, high pressure balloon catheters commercially available today generally have expanded diameters no exceeding 12 mm. Accordingly, such devices cannot generally be used in larger diameter vessels, such as the pulmonary artery, aorta, or hollow-body organs, because at larger diameters the balloons tend to bulge locally and lose their strength, facilitating rupture.

In view of the shortcomings of previously known dilatation devices, it would be desirable to provide apparatus and methods for dilating a vessel that permit dilatation of certain hardened stenoses using higher pressures than heretofore attainable.

It also would be desirable to provide apparatus and methods for dilating vessels using balloon elements that allow the use of higher pressures than available in previously known devices, and that reduce the risk of vessel dissection resulting from balloon rupture.

It further would be desirable to provide apparatus and methods of dilating large diameter vessels having diameters from 15 to 35 mm, such as the aorta and pulmonary artery, but which apparatus are less prone to localized bulging, thereby reducing the risk of rupture.

SUMMARY OF THE INVENTION

In view of the foregoing, it is an object of this invention to provide apparatus and methods for dilating a vessel that permit dilatation of certain hardened stenoses using higher pressures than heretofore attainable.

It is another object of this invention to provide apparatus and methods for dilating vessels using balloon elements that allow the use of higher pressures than available in previously known devices, and that reduce the risk of vessel dissection resulting from balloon rupture.

It is a further object of the present invention to provide apparatus and methods of dilating large diameter vessels, such as the aorta and pulmonary artery, with reduced risk of rupture of the dilatation element.

These and other objects of the present invention are accomplished by providing apparatus and methods for dilating vessels, including large diameter vessels and hollow-body organs, with a balloon element and sheath capable of withstanding high pressures, with reduced risk of catastrophic rupture.

In one preferred embodiment of the apparatus of the present invention, a catheter having a balloon element is disposed within a sheath having an expandable but non-compliant mesh region covering the balloon element. In accordance with the present invention, the sheath is selected from among a plurality of sheaths each having a mesh member that is expandable to a different predetermined diameter. The expandable mesh region prevents the balloon member from developing bulges during inflation, and constrains the edges of the balloon from dissecting or rupturing the vessel in the event of balloon rupture. The sheath, which extends to a proximal end of the catheter, is also employed to reduce the diameter of the balloon member following the dilatation procedure, thereby preventing the balloon from bunching up in the vessel or organ.

In alternative embodiments, a plurality of sheaths having mesh regions of different predetermined expanded diameters may be provided as separate elements designed to be used in conjunction with any previously known balloon catheters, so that a previously known catheter may be modified for use in treating hardened stenoses or larger diameter vessels. Methods of using the apparatus of the present invention to dilate vessels and organs are also provided.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

The present invention relates generally to apparatus and methods for dilating vessels and hollow-body organs, and more particularly, for dilating vessels and hollow-body organs having large diameters or hardened constrictions. The present invention is intended not only to permit the use of higher pressures than heretofore typically employed, but also reduces the risk of vessel dissection caused by balloon rupture.

Figure 1:
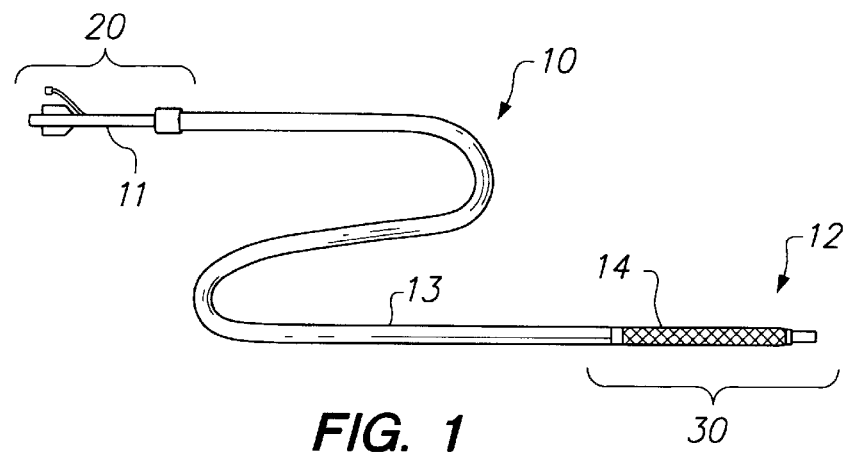
FIG. 1 is a side view of an illustrative embodiment of apparatus constructed in accordance with the present invention.

Referring to FIG. 1, illustrative apparatus 10 constructed in accordance with the present invention is described. Apparatus 10 includes catheter 11 having balloon element 12 and sheath 13 having expandable but non-compliant mesh 14 disposed over balloon element 12. In accordance with the present invention, apparatus 10 may be provided wherein the non-compliant mesh may be selected from among a plurality, in which each non-compliant mesh has a different predetermined expanded diameter.

Figure 2:
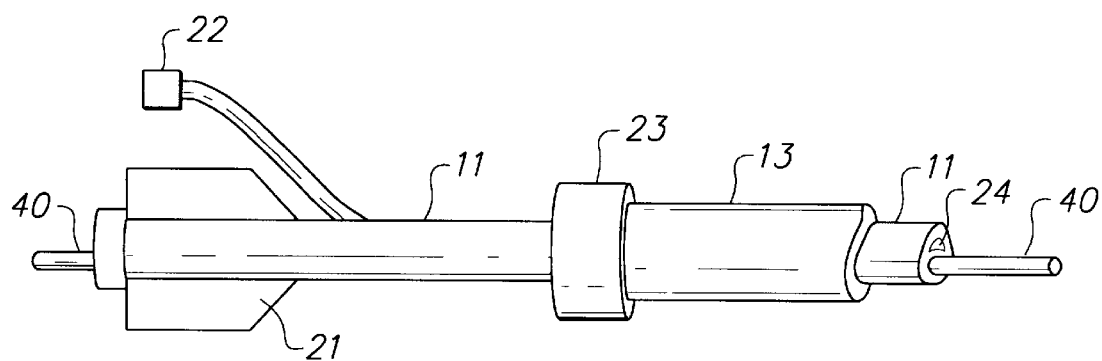
FIG. 2 is a side view of the proximal end of the apparatus of FIG. 1.
Figure 4:
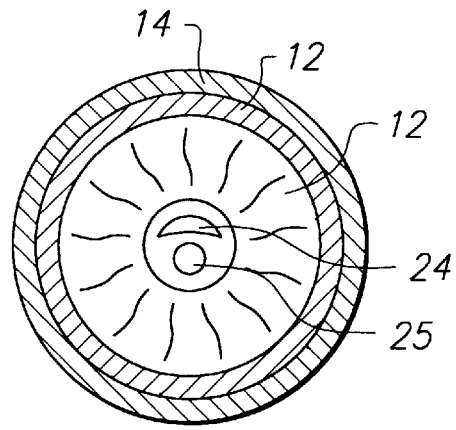
FIG. 4 is a cross-sectional view of the distal end of the apparatus of FIG. 1 in an inflated state, taken along view line 4—4 in FIG. 3.

As shown in greater detail in FIG. 2, apparatus 10 includes proximal region 20 including luer 21 for manipulating catheter 11, inflation port 22, and sheath retractor ring 23. As best shown in FIG. 4, catheter 11 includes inflation lumen 24 that extends between inflation port 22 and the interior of balloon element 12, and guidewire lumen 25 that illustratively extends from the proximal end to the distal end of catheter 11 to accept guidewire 40. Sheath 13 is slidably disposed on catheter 11 so that it may slide in a distal direction upon inflation of balloon element 12, and may be pulled by the clinician in the proximal direction by retractor ring 23 once the balloon element has been deflated.

Figure 3:
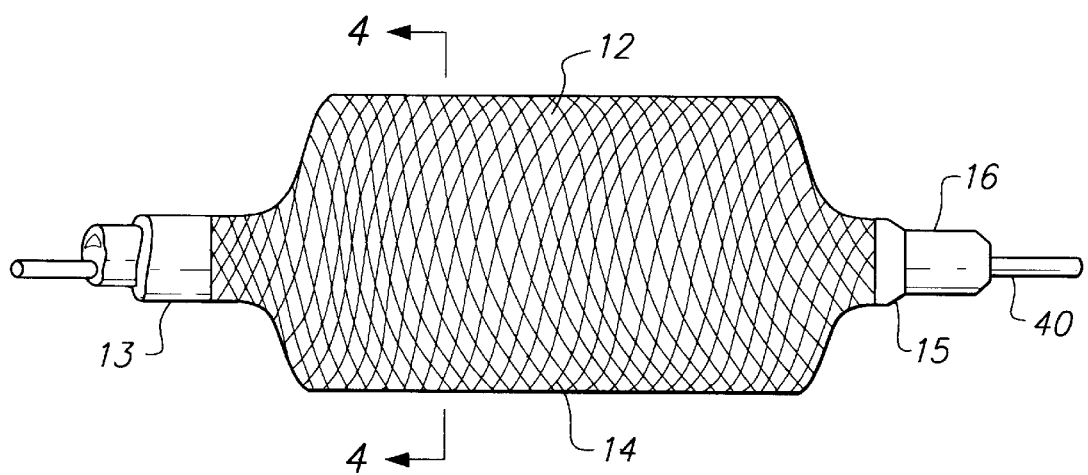
FIG. 3 is a side view of the distal end of the apparatus of FIG. 1.

Referring to FIG. 3, sheath 13 is joined in distal end region 30 to expandable mesh 14. Expandable mesh 14 includes rigid retainer ring 15 disposed from the distal end of expandable mesh 14 that engages distal end 16 of catheter 11. Rigid retainer ring 15 maintains expandable mesh 14 aligned with balloon member 12, and prevents proximal force on retractor knob 23 from pulling the expandable mesh to a position proximal to balloon element 12. Sheath 13 is shorter than catheter 11 so that, when sheath 13 is disposed over catheter 11, retraction of retractor knob 23 in the proximal direction will not interfere with inflation port 22.

As shown in FIG. 4, expandable mesh 14 contacts the exterior surface of balloon element 12. Expandable mesh 14 comprises a very low compliance material, such as a monofilament polyester mesh, or a mesh formed of stainless steel, Kevlar® (a fiber produced from poly-paraphenylene terephthalamide, sold by E. I. DuPont de Nemours, Wilmington, Del.), nickel-titanium alloy or other high strength material, so that the maximum inflated size of the device is determined by the predetermined expanded diameter of mesh 14. The filaments of expandable mesh 14 move with respect to one another so that upon inflation of the balloon element, the mesh 14 expands and pulls sheath 13 and retractor ring 23 in the distal direction. After balloon element 12 is deflated, expandable mesh 14 may be returned to its contracted state by pulling proximally on retractor ring 23.

It is contemplated that use of sheath 13 and expandable mesh 14, in conjunction with previously known balloon catheters, will enable the balloons of those devices to be inflated to twice or more the rated burst pressures, without rupture. For example, applicant has determined that a balloon having a rated pressure of 5 atmosphere may be safely inflated to about 25–30 atm without rupture. In addition, by selection of a desired predetermined expanded diameter of mesh 14, it is expected that balloons of previously known catheters may be inflated to diameters twice or more larger than the rated diameters of those balloons when used with the sheath and expandable mesh of the present invention, again without rupture.

It is further contemplated that expandable mesh 14 of the present invention imposes a radial and longitudinal stress on the balloon element during inflation that tends to equalize the circumferential and longitudinal stresses developed in the balloon member. This equalization of stresses around the balloon element is expected to reduce the risk of bulging and concomitant localized loss of strength of the balloon element. Moreover, expandable mesh 14 serves to confine the edges of balloon element 12 in those few cases where the balloon does rupture, thereby reducing the risk of dissection of a vessel caused by rupture, and trapping any pieces of the perforated balloon element.

In a preferred embodiment of the present invention, catheter 11 and balloon element 12 may comprise materials commonly used in previously known balloon catheters, e.g., polyethylene or PET. Balloon element 12 may also comprise a compliant material, such as nylon. Sheath 13 preferably comprises a material commonly used in catheter construction, such as polyethylene or polyvinylchloride, while expandable mesh 14 preferably comprises a structure woven from polyethylene strands (i.e., monofilament polyester mesh). Alternatively, expandable mesh 14 may comprises strands of another polymer, Kevlar®, stainless steel, nickel-titanium alloy or other high strength material. Preferably, the cross-points of the mesh are not interconnected, so that the strands may slide freely over one another when balloon element 12 is inflated. Sheath 13 and retainer ring 15 may be joined to expandable mesh 14 using any suitable method, such as thermowelding or biocompatible adhesive.

Operation of apparatus 10 of the present invention is now described for dilating a vessel. Typically, guidewire 40 first is disposed across a stenosis using an introducer catheter, as is well known in the art. Retractor knob 23 of sheath 13 is pulled in the proximal direction to elongate expandable mesh 14, and apparatus 10 is then advanced along guidewire 40 so that balloon element 12 is disposed across the stenotic region under fluoroscopic guidance, as determined, for example, using radio-opaque markers contained within balloon element 12.

Balloon element 12 is then inflated via lumen 24 and inflation port 22. In accordance with the methods of the present invention, balloon element 12 is inflated to until constrained by expandable mesh 14, which in turn will expand only to its predetermined expanded diameter, and no further. Balloon element 12 may be expanded to twice or more its rated pressure, or twice or more its rated diameter, without bulging or rupture. As balloon element 12 expands, expandable mesh 14 opens to its predetermined expanded diameter, thereby causing disruption of the stenosis (e.g., compressing or cracking plaque to restore the patency of the vessel or organ).

Upon completion of the step of dilating the vessel, as determined, for example, by angiography, balloon element 12 is deflated. The clinician then grasps retractor knob 23, and while holding catheter 11 steady using luer 21, pulls retractor knob 23 in the distal direction, thereby contracting expandable mesh 14 to approximately its initial diameter. Apparatus 10 may then be withdrawn proximally from the patient's vessel or organ.

Figure 5:
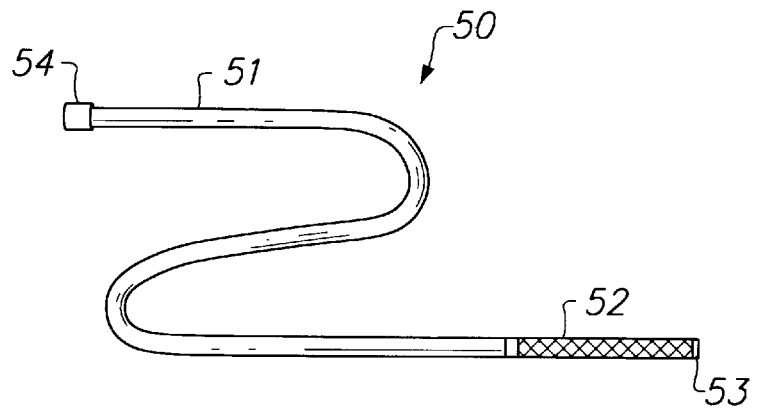
FIG. 5 is a side view of an illustrative embodiment of the sheath of the present invention to be used with conventional angioplasty balloon catheters.

With respect to FIG. 5, apparatus 50 constructed in accordance with the present invention is described. Apparatus 50 comprises sheath 51, expandable mesh 52, retainer ring 53 and retractor knob 54. Apparatus 50 is constructed as described hereinabove with respect to the similar components of apparatus 10 of FIG. 1, and is intended to be used with commercially available, previously known, balloon catheters. In particular, apparatus 50 is intended to be slipped onto a previously known catheter to provide the same benefits as apparatus 10 of FIG. 1. Retainer ring 53 is sized so that it engages the distal neck of the balloon element, and thus cannot be pulled too far in the proximal direction (i.e., retainer ring 53 keeps expandable mesh 52 aligned with and disposed over the balloon element).

Figure 6:
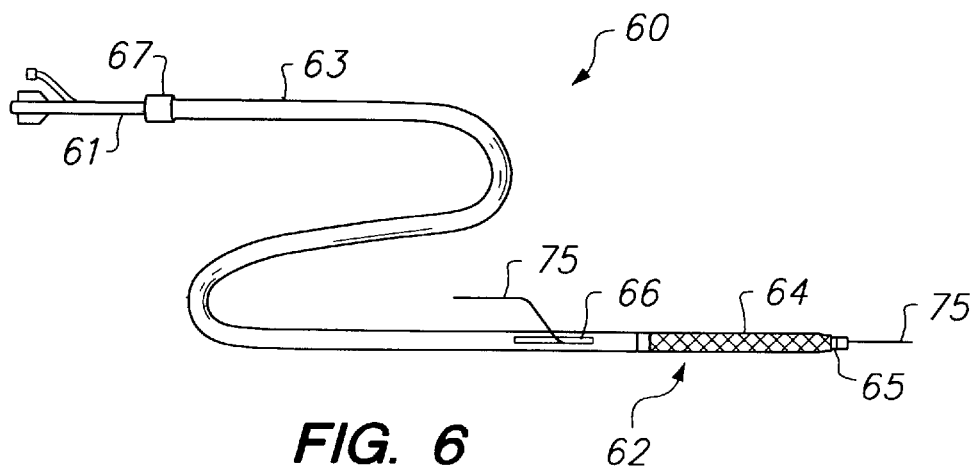
FIG. 6 is a side view of an illustrative embodiment of the present invention for use with rapid exchange type catheters.

Referring now to FIG. 6, apparatus 60 constructed in accordance with the present invention is described. Apparatus 60 differs from that of FIG. 1 in that the guidewire lumen extends only within distal region 70 of catheter 61, with the guidewire lumen exiting from the circumferential surface of the catheter proximal of balloon element 62. Catheter 61 may therefore be used in a rapid exchange mode, as described, for example, in Yock U.S. Pat. No. 5,040,548, which is incorporated herein by reference.

Apparatus 60 includes sheath 63 having expandable mesh 64 and retainer ring 65. In accordance with this aspect of the invention, sheath 63 includes an elongate aperture or slit 66 through which guidewire 75 exits sheath 63. In this manner, sheath 63 is free to move distally (upon inflation of balloon element 63) or proximally (when pulled by retractor knob 67), without interfering with guidewire 75.

While preferred illustrative embodiments of the invention are described above, it will be apparent to one skilled in the art that various changes and modifications may be made therein without departing from the invention, and the appended claims are intended to cover all such changes and modifications that fall within the true spirit and scope of the invention.

What is claimed is:

1. Apparatus for dilating a vessel or organ comprising:
    a catheter shaft having proximal and distal ends;
    a balloon disposed on the distal end of the catheter shaft;
    a sheath disposed surrounding the catheter shaft, the sheath having proximal and distal ends; and
    a mesh portion attached to the distal end of the sheath and disposed surrounding the balloon for sliding movement relative thereto, the mesh portion comprising a non-compliant material having a first state wherein the mesh portion has a first length and an insertion diameter and a second state wherein the mesh portion has second length, shorter than the first length, and a selected predetermined expanded diameter; and
    a retractor element disposed on the proximal end of the sheath for retracting the mesh portion to the first state,
    wherein, when the balloon is fully inflated, the mesh portion is in the second state and attains the selected predetermined expanded diameter, the mesh portion constraining the balloon from further expansion.

2. The apparatus as defined in claim 1 wherein the mesh portion enables the balloon to be expanded to at least twice a rated burst pressure of the balloon.

3. The apparatus as defined in claim 1 wherein the mesh portion enables the balloon to be inflated to at least twice a rated inflation pressure of the balloon.

4. The apparatus as defined in claim 1 wherein the mesh portion has a distal end, the apparatus further comprising:
    a retainer ring disposed on the distal end of the mesh portion, the retainer ring engaging the catheter at a position distal of a distal neck of the balloon.

5. The apparatus as defined in claim 1 wherein the catheter is configured for use with a guidewire in a rapid exchange modality, the apparatus further including an elongated aperture in the sheath proximal of the mesh portion, the guidewire passing through the elongated aperture.

6. The apparatus as defined in claim 1 wherein the balloon comprises a material selected from the group consisting of: a compliant material and a minimally-compliant material.

7. The apparatus as defined in claim 1 wherein the mesh portion comprises a material selected from the group consisting of: a monofilament polyester material, Kevlar®, stainless steel and a nickel-titanium alloy.

8. A kit for dilating a vessel or organ comprising:
    a catheter comprising a shaft having proximal and distal ends and a balloon disposed on the distal end of the shaft; and
    a sheath selected from among a plurality of sheaths, each one of the plurality of sheaths including a mesh portion having a predetermined expanded diameter, each one of the sheaths comprising:
        a tubular member having proximal and distal ends, the tubular member disposed surrounding the shaft;

a mesh portion attached to the distal end of the tubular member and disposed surrounding the balloon for sliding movement relative thereto, the mesh portion comprising a non-compliant material having a first state wherein the mesh portion has a first length and an insertion diameter and a second state wherein the mesh portion has second length, shorter than the first length, and a predetermined expanded diameter; and a retractor element disposed on the proximal end of the tubular member for retracting the mesh portion to the first state, wherein, when the balloon is fully inflated, the mesh portion of the selected one of the plurality of sheaths is in the second state and attains the predetermined expanded diameter, the mesh portion constraining the balloon from further expansion.

9. The kit as defined in claim 8 wherein the mesh portion of at least one of the plurality of sheaths enables the balloon to be expanded to at least twice a rated diameter of the balloon.

10. The apparatus as defined in claim 8 wherein the mesh portion of at least one of the plurality of sheaths enables the balloon to be inflated to at least twice a rated inflation pressure of the balloon.

11. The apparatus as defined in claim 8 wherein the mesh portion of at least one of the plurality of sheaths has a distal end, the apparatus further comprising:

a retainer ring disposed on the distal end of the mesh portion, the retainer ring engaging the shaft at a position distal of a distal neck of the balloon.

12. The apparatus as defined in claim 8 wherein the catheter is configured for use with a guidewire in a rapid exchange modality, at least one of the plurality of sheaths further including an elongated aperture in the tubular member proximal of the mesh portion, the guidewire passing through the elongated aperture.

13. The apparatus as defined in claim 8 wherein the balloon comprises a compliant material.

14. The apparatus as defined in claim 8 wherein the mesh portion of at least one of the plurality of sheaths comprises a monofilament polyester material.

15. A method of dilating a constriction in a vessel or organ, the method comprising steps of:

providing apparatus comprising a catheter a distal end and a balloon disposed on the distal end and a sheath disposed on the catheter, the sheath including a mesh portion aligned with and surrounding the balloon, the mesh portion arranged for sliding movement relative to the balloon, the mesh portion comprising a non-compliant material having a first state wherein the mesh portion has a first length and an insertion diameter and a second state wherein the mesh portion has second length, shorter than the first length, and a selected predetermined expanded diameter;

pulling the sheath in a proximal direction so that the mesh portion assumes the first state;

inserting a guidewire into the vessel or organ;

advancing the apparatus along the guidewire to position the mesh portion and balloon within the constriction; and inflating the balloon so that the mesh portion expands to the second state and attains the selected predetermined diameter to disrupt the constriction, the mesh portion constraining the balloon from further expansion.

16. The method as defined in claim 15 wherein the step of inflating the balloon comprises a step of inflating the balloon to a diameter at least twice a rated burst pressure of the balloon.

17. The method as defined in claim 15 wherein the step of inflating the balloon comprises a step of inflating the balloon to a pressure at least twice a rated pressure of the balloon.

18. The method as defined in claim 15 further comprising steps of:

deflating the balloon; and retracting the sheath so that the mesh portion attains the first state; and retracting the apparatus from the vessel or organ along the guidewire.

19. The method as defined in claim 18 wherein the step of retracting the sheath causes the balloon to attain a compressed diameter.

20. The method as defined in claim 15 wherein the step of providing the apparatus comprises steps of:

obtaining the catheter;

obtaining the sheath; and inserting the catheter within the sheath so that the mesh portion is aligned with the balloon.

* * * * *